United States Patent [19]

Sherman et al.

[11] Patent Number: 5,782,831
[45] Date of Patent: Jul. 21, 1998

[54] METHOD AN DEVICE FOR SPINAL DEFORMITY REDUCTION USING A CABLE AND A CABLE TENSIONING SYSTEM

[75] Inventors: Michael C. Sherman; Troy D. Drewry, both of Memphis, Tenn.

[73] Assignee: SDGI Holdings, Inc., Memphis, Tenn.

[21] Appl. No.: 744,616

[22] Filed: Nov. 6, 1996

[51] Int. Cl.$^6$ .............................. A61B 17/56; A61B 17/58
[52] U.S. Cl. .............................. 606/61; 606/72; 606/73; 606/103
[58] Field of Search ............................ 606/61, 72, 73, 606/74, 103, 113; 254/264, 324, 881, 882, 883; 439/881, 882, 883

[56] References Cited

U.S. PATENT DOCUMENTS

| | | | |
|---|---|---|---|
| 1,874,593 | 8/1932 | Olson | 439/883 |
| 4,047,523 | 9/1977 | Hall | 606/61 |
| 4,590,928 | 5/1986 | Hunt et al. | 606/72 |
| 4,611,581 | 9/1986 | Steffee. | |
| 4,790,303 | 12/1988 | Steffee. | |
| 4,805,602 | 2/1989 | Puno et al. | 606/61 |
| 5,092,868 | 3/1992 | Mehdian. | |
| 5,156,616 | 10/1992 | Meadows et al. | 606/73 |
| 5,242,446 | 9/1993 | Steffee et al.. | |
| 5,254,118 | 10/1993 | Mirkovic | 606/61 |
| 5,304,178 | 4/1994 | Stahurski. | |
| 5,312,410 | 5/1994 | Miller et al.. | |
| 5,395,374 | 3/1995 | Miller et al.. | |
| 5,417,690 | 5/1995 | Sennett et al. | 606/61 |
| 5,423,818 | 6/1995 | Van Hoeck et al.. | |
| 5,545,163 | 8/1996 | Miller et al. | 606/72 |

OTHER PUBLICATIONS

*Atlas of Spinal Operations*, Thieme, pp. 114–129. ISBN 3-13-114001-1 (GTV). ISBN 0-86577-496-X (TMP).
*CD Cotrel–Dubousset Instrumentation Chopin Plate "improvement of the vertebral grip"*, Sofamor Spine Division.
*LSF Lumbosacral Fixator*, HospTech Aktie Bolag. Villa Malmen, 740 11 Lannaholm, Sweden. Edition Sep.–91. *Surgical Technique Step 9*, p. 22.
*Edwards Instrumentation: A Modular Spinal System*, Charles C. Edwards, pp. 303–324.
*Spinal Instrumentation*, pp. 210–217.

*Primary Examiner*—Michael Buiz
*Assistant Examiner*—Julian W. Woo
*Attorney, Agent, or Firm*—Woodard, Emhardt, Naughton Moriarty & McNett

[57] ABSTRACT

A reduction system and method is disclosed for reducing a displaced vertebra between adjacent vertebrae. The system can include an anchor 60 placed in the displaced vertebra 70b, a cable 11 attached to the anchor 60 and a clamping member 50 which can selectively engage or disengage the cable 11 to maintain its position. The clamping member can be seated in a rod connector 58 attached to a rod 80 running along the longitudinal axis of the spinal column. A tensioning force can be applied to the cable 11 to pull vertebra 70b toward the rod 80. Once the vertebra 70b is pulled into the desired position, the anchor can be secured to the rod to maintain the position of the vertebra and the reduction apparatus is removed.

31 Claims, 12 Drawing Sheets

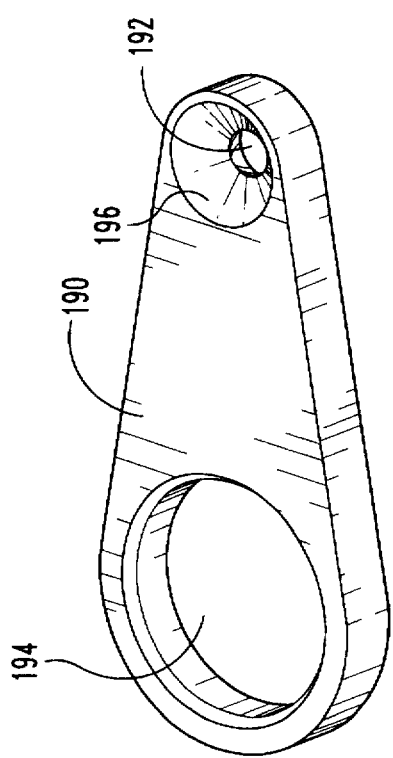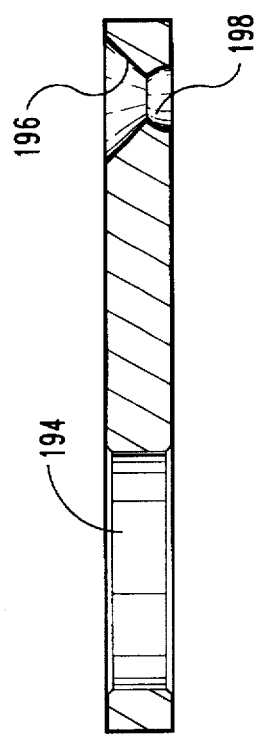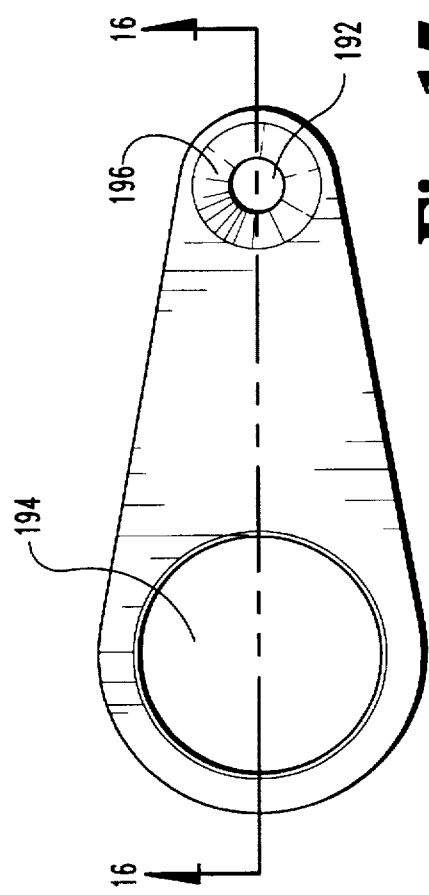

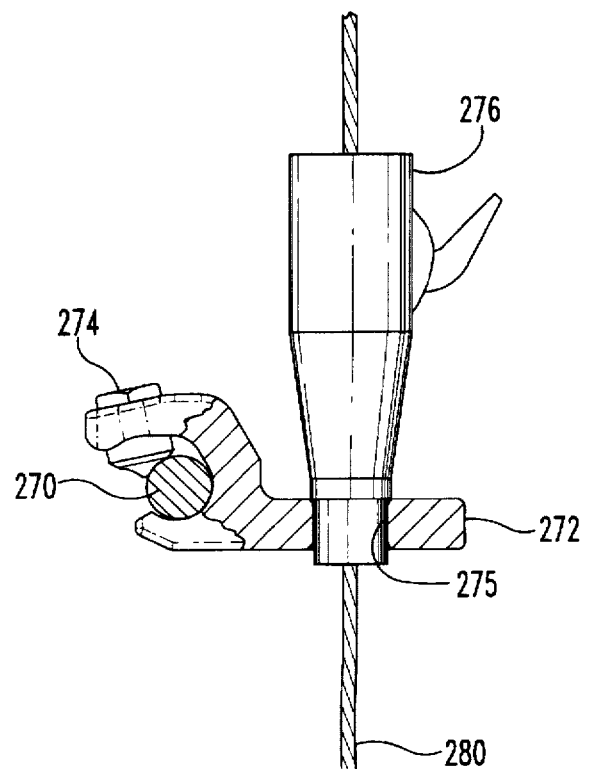
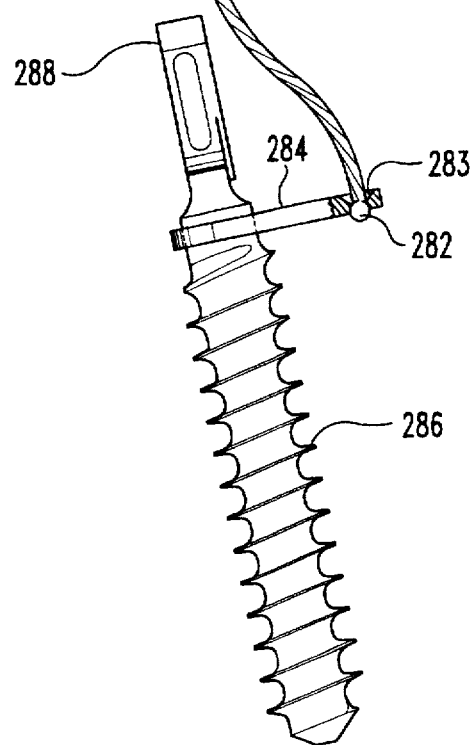
Fig. 19

METHOD AN DEVICE FOR SPINAL DEFORMITY REDUCTION USING A CABLE AND A CABLE TENSIONING SYSTEM

BACKGROUND OF THE INVENTION

This invention relates generally to orthopaedics and spinal surgery, and more particularly to a method and apparatus for straightening a spinal column by reducing the extent of displacement between adjacent vertebrae.

In many cases of deformity, such as spondylolisthesis, it is desirable to reduce the extent of displacement of a vertebra prior to fusion to adjacent vertebra. A spondylolistesis reduction can be a technically demanding procedure requiring great care to prevent neurological impairment and damage to surrounding soft tissue. Several systems have been utilized to accomplish a necessary reduction.

An early effort at spondylolisthesis reduction utilized a cable system to apply force to the displaced vertebra. In this system one end of an extremely long cable was anchored to a vertebra and the other end was threaded through a fixture attached to the ceiling and included a series of traction weights positioned on the cable. Such a system utilizing long cables and weights external to the operating field proved unwieldy and bulky. Moreover, the surgeon could not quickly and effectively control the force applied to the vertebra.

In addition to the cable system described above, systems utilizing threaded shafts to draw the vertebra upwards are well known. One such apparatus for use in straightening a spinal column in a human by the reduction of a displacement between adjacent vertebrae is disclosed in U.S. Pat. No. 4,611,581. The apparatus disclosed in this patent includes a pair of rigid plates positioned along the spinal column with a double threaded screw anchored in the vertebrae requiring alignment with the vertebral column. The lower portion of the screw has a cancellous thread which engages the bone, while the upper portion has a machine thread which passes through a slot in the plate and is capable of receiving an internally threaded nut. Upon rotation of the internally threaded nut bearing against the plate, the misaligned vertebra is drawn toward the plate as the nut advances over the machine threads of the screw. This system requires that the machine threaded end of the screw extend through a relatively narrow slot in the plate. Such a requirement may limit the surgeon's ability to properly place the screw or may require manipulation of the vertebrae to align the screw with the slot in the plate. Additionally, for high grade spondylolisthesis the machine threaded portion must be extremely long to accomplish the reduction and once the vertebra is properly aligned, the excess machine threaded portion is trimmed leaving a coarse edge which may irritate surrounding tissue.

Other systems have utilized a separate threaded shaft to draw the vertebrae into alignment. In such systems, the bone screw does not include a machine threaded portion. Instead, a separate reduction mechanism grasps the head on the screw and is braced against a rod. A threaded shaft attached to the screw head pulls the misaligned vertebra toward the rod. Here again, the devices are cumbersome and difficult to maneuver into the appropriate position so the vertebrae is pulled in the desired direction. Also, many of these systems are composed of relatively large components, making the apparatus unduly bulky.

SUMMARY OF THE INVENTION

The present invention contemplates a deformity reduction apparatus. The contemplated system utilizes an anchor element connected to an elongated member, the anchor element is secured placed in a vertebra displaced from the remainder of the vertebral column. The elongated member extends through a clamping member which can selectively engage or disengage the elongated member to maintain its position. The clamping member is positioned on a longitudinal member which is positioned along the longitudinal axis of the spine. A pulling force is applied to the elongated member to pull the vertebra toward the longitudinal member. The clamping member bears against the longitudinal member and clamps the elongated member to maintain the position of the vertebra.

In some applications, the clamping device may not be necessary and the elongated member can be passed through a tensioning tool which bears against the longitudinal member. Here again, applying tension to the elongated member pulls the displaced vertebra toward the longitudinal member.

In the present invention, it is contemplated that once the displaced vertebra is in the desired position, the reduction apparatus is removed and the anchor secured to the longitudinal member. Additionally, where the longitudinal member is an elongated rod, it is contemplated that the clamp may engage a rod connector attached to the rod.

Moreover, the combination of a tensioning tool having a calibrated scale indicating the amount of pulling force placed on a cable and a clamping device, allows performance of the reduction in a slow, controlled manner. Additionally, the flexibility of the cable and various attachment constructions disclosed herein permit pulling the anchor at various angles to the longitudinal axis of the anchor.

One object of the present invention is to provide a reduction apparatus that can pull a displaced vertebra in various directions regardless of the orientation of an anchoring element.

Another object of the present invention is to provide a reduction apparatus utilizing a cable tensioning tool that applies measured force to the cable.

Another object of the present invention is to provide a reduction apparatus that can utilize a variety of anchoring elements and is adaptable to numerous spinal systems.

Another object of the present invention is to provide a reduction apparatus that can reduce a high grade displacement in a controlled manner.

Still another object of the present invention is to provide an improved reduction apparatus.

Other objects and advantages of the present invention will be apparent from the following description.

3

Figure 8:
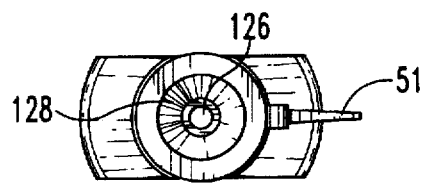

FIG. 8 is a top view of the clamp and clamp fixture.

Figure 9:
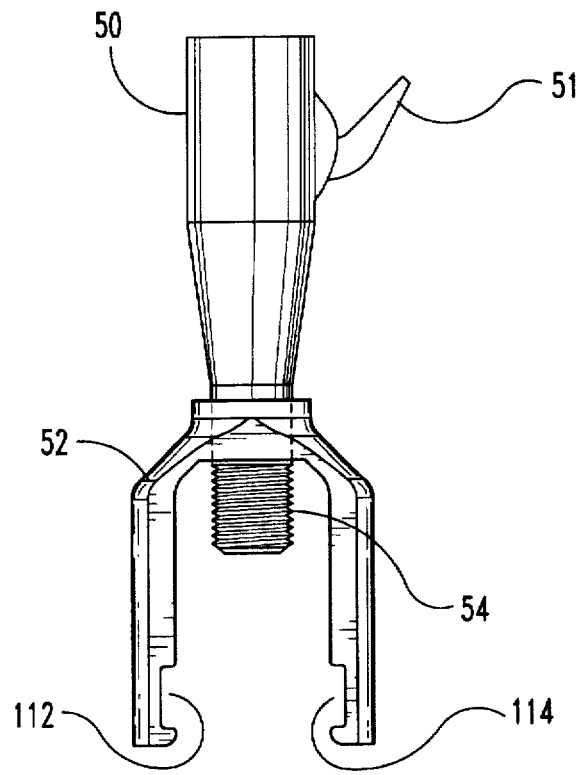

FIG. 9 is a front view of the clamp mounted in the and clamp fixture.

Figure 10:
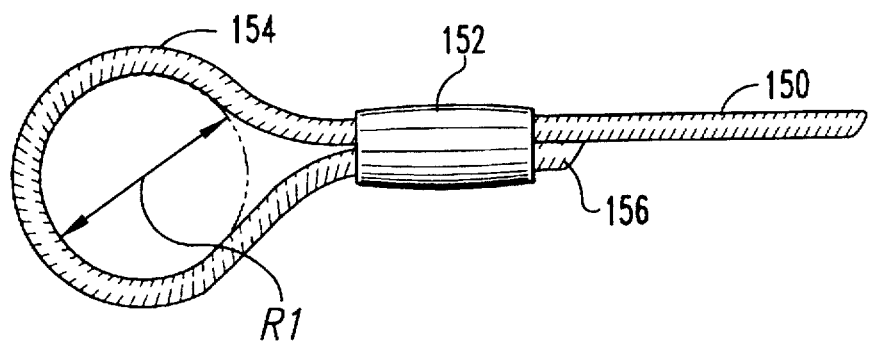

FIG. 10 is a top view of a cable with a loop formed at one end.

Figure 11:
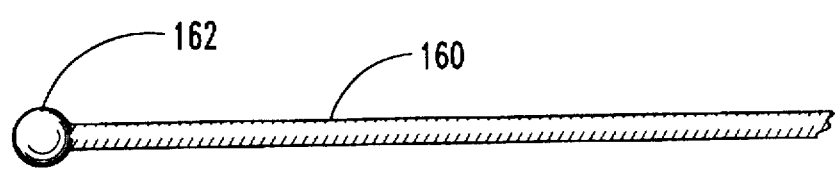

FIG. 11 is a top view of a cable with an enlarged ball at one end.

Figures 12, 13:
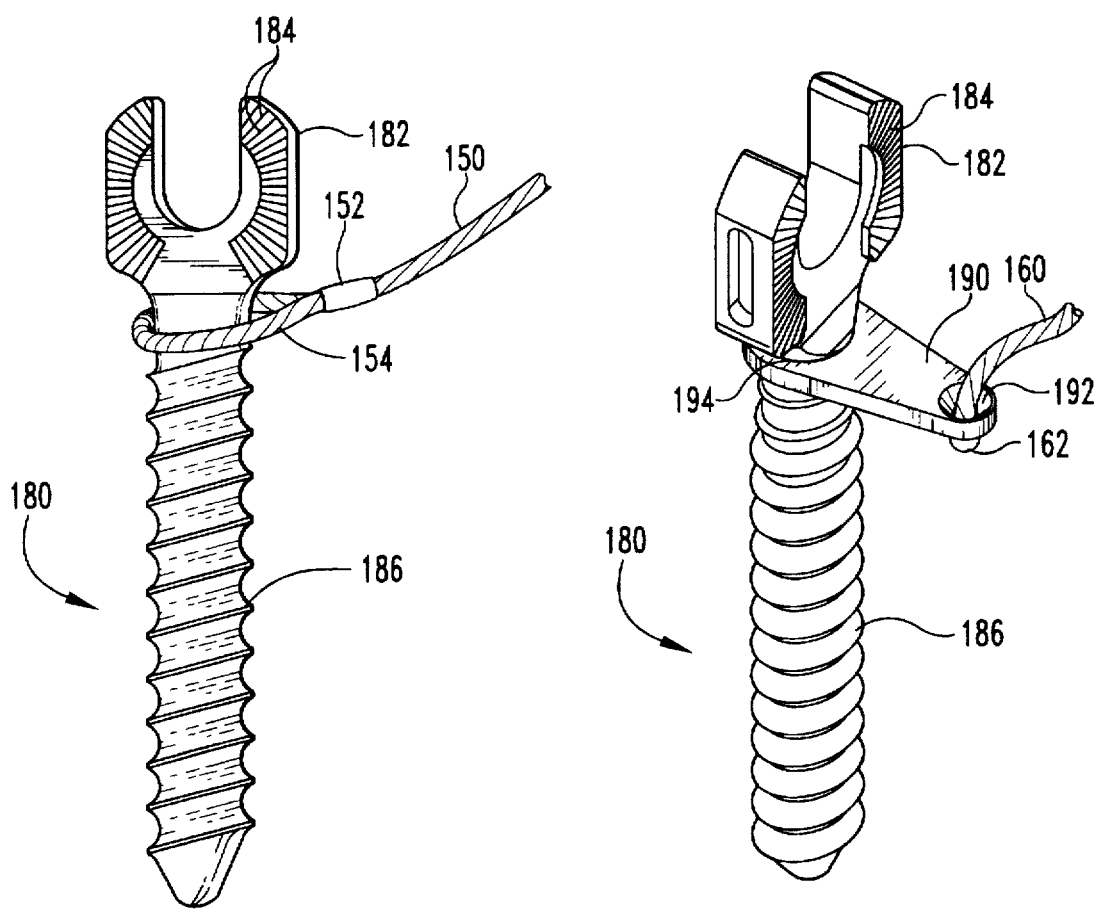

FIG. 12 is a front view of a bone screw with the looped cable of FIG. 10 positioned below the enlarged head of the bone screw according to another embodiment of the invention.

FIG. 13 is a bone screw with an attachment plate positioned below the enlarged head according to a further embodiment of the invention.

FIG. 14 is a perspective view of the attachment plate of FIG. 13.

FIG. 15 is a top view of the attachment plate of FIG. 13.

FIG. 16 is a cross sectional side view of the attachment plate of FIG. 15 taken along line A—A.

Figure 17:
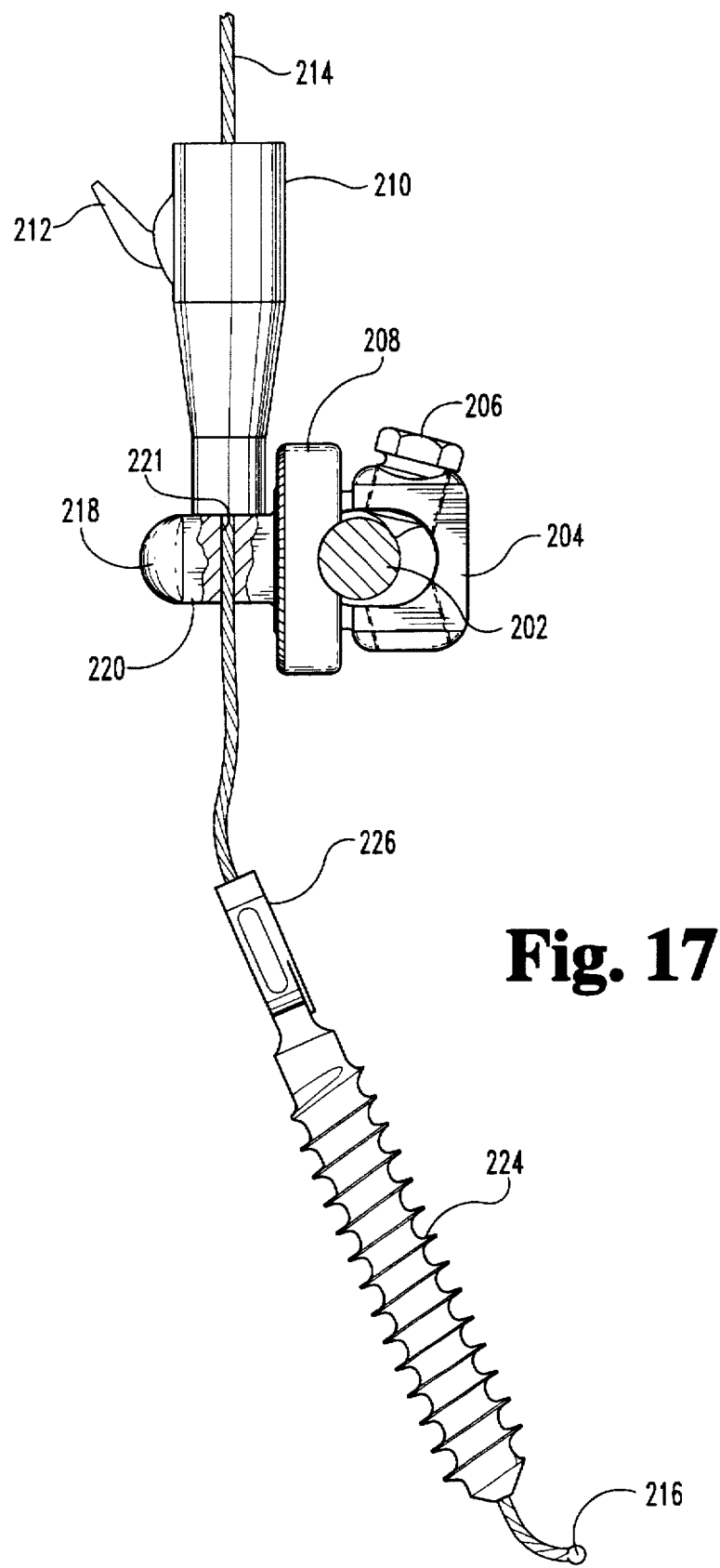

FIG. 17 is a schematic illustration of the application of a tensioning apparatus according to a second embodiment of the invention.

Figure 18:
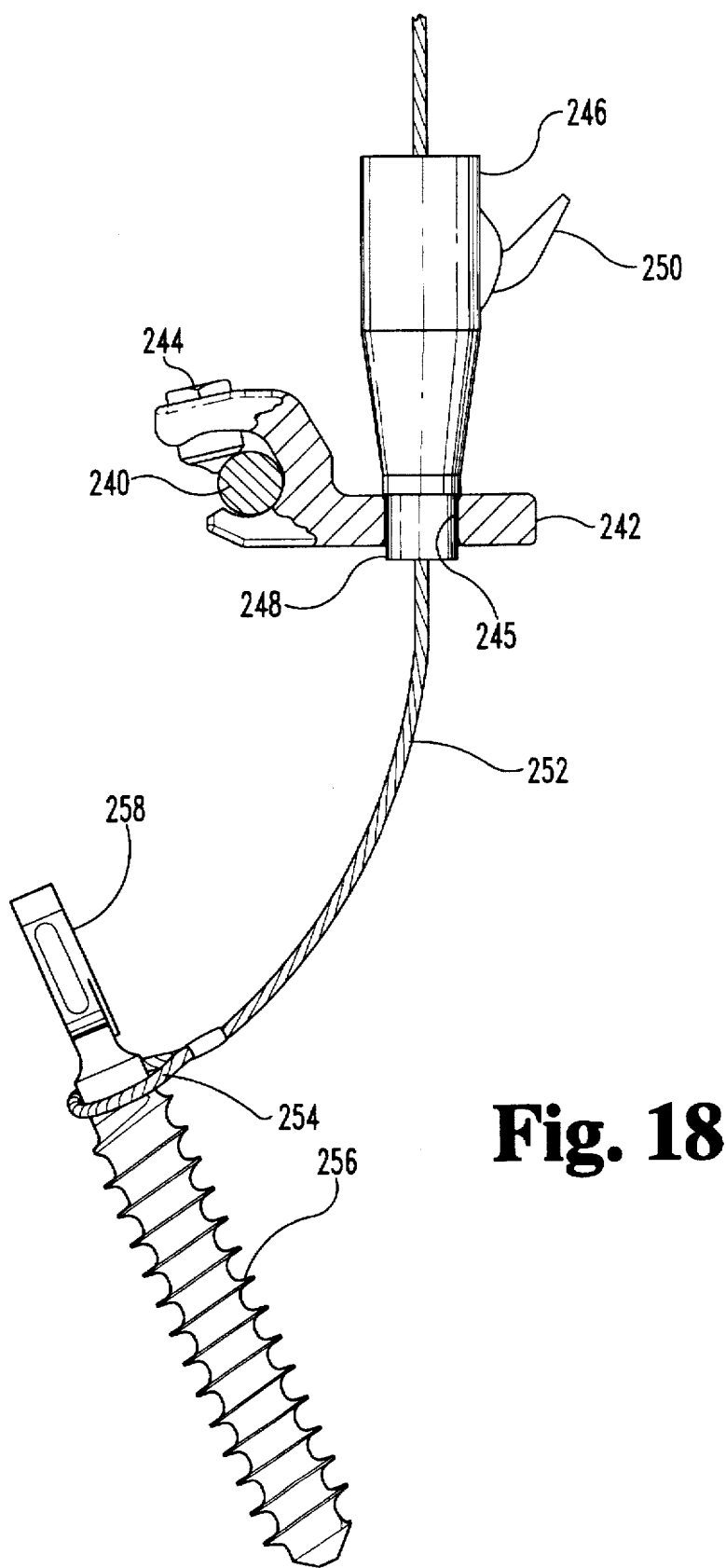

FIG. 18 is a schematic illustration of the application of a tensioning apparatus according to a third embodiment of the invention.

FIG. 19 is a schematic illustration of the application of a tensioning apparatus according to a fourth embodiment of the invention.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
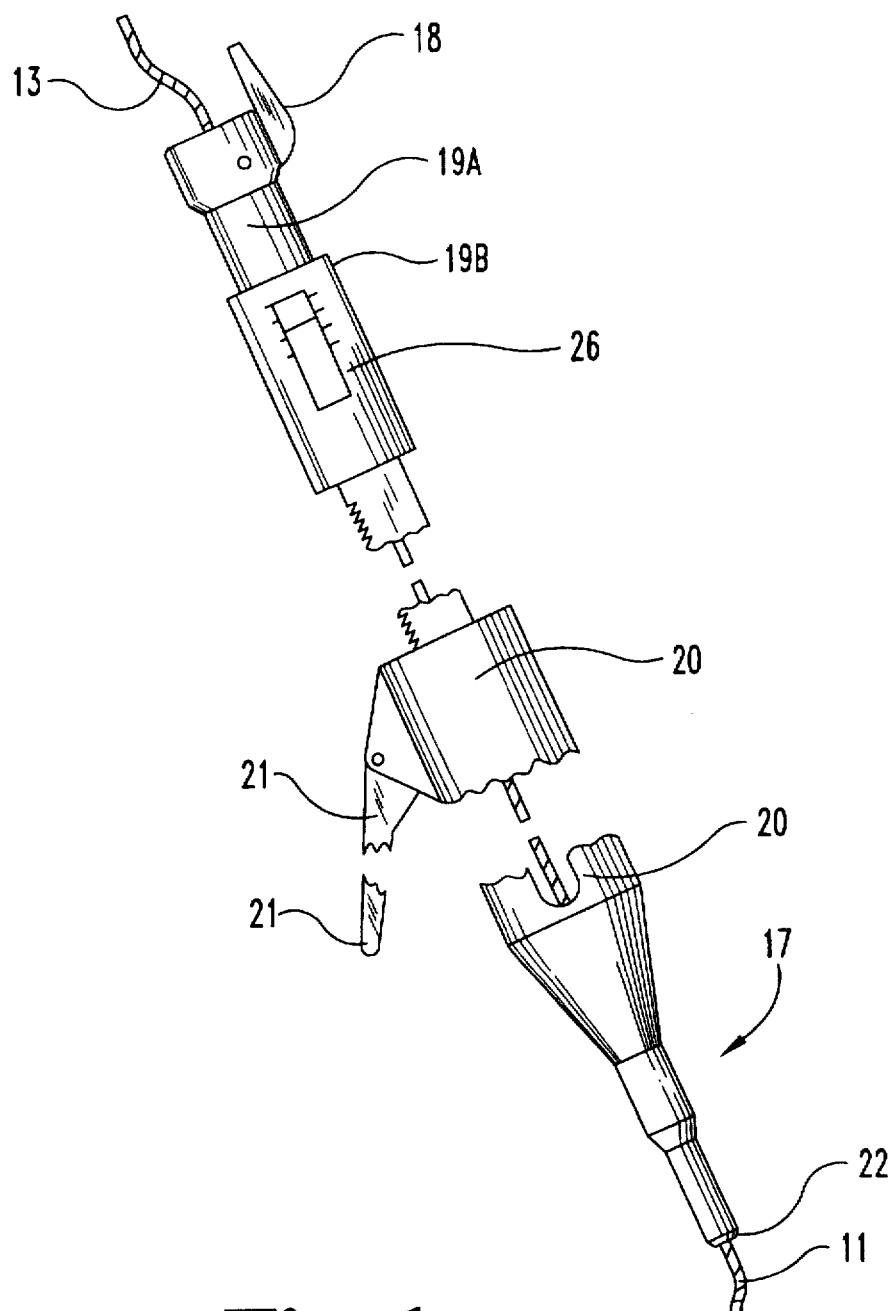
FIG. 1 is an illustration of a known cable tensioning tool.

Referring now to the drawings in detail, and more particularly to FIG. 1, the present invention requires some type of pulling force to move the misaligned vertebra into alignment with the adjacent vertebrae. Although it is contemplated that only pulling force could be used. FIG. 1 shows a well known tensioning tool capable of providing the pulling force required to pull the misaligned vertebra into a desired position. This type of tensioning tool is more fully explained in U.S. Pat. No. 5,312,410 and the description therein is incorporated by reference. In operation, cable 11 is passed through the central passageway in tensioning tool 17 until free end 13 extends beyond tensioning tool 17. Lug clamp 18 at the upper end of tensioning tool 17 clamps a portion 19A of the tensioning tool onto the cable. Portion 19A telescopes within portion 19B which is secured to a bar which telescopes into the barrel 20 of the tensioning tool and, upon operation of the hand lever 21, portion 19B is ratcheted out of the barrel 20. Further ratcheting of the tool pulls the cable up until the desired tension is reached, as indicated on the scale 26 on portion 19B in which portion 19A is restrained by calibrated spring. The calibrated tensioning tool permits controlled application of tensioning force on cable 11.

Figure 2:
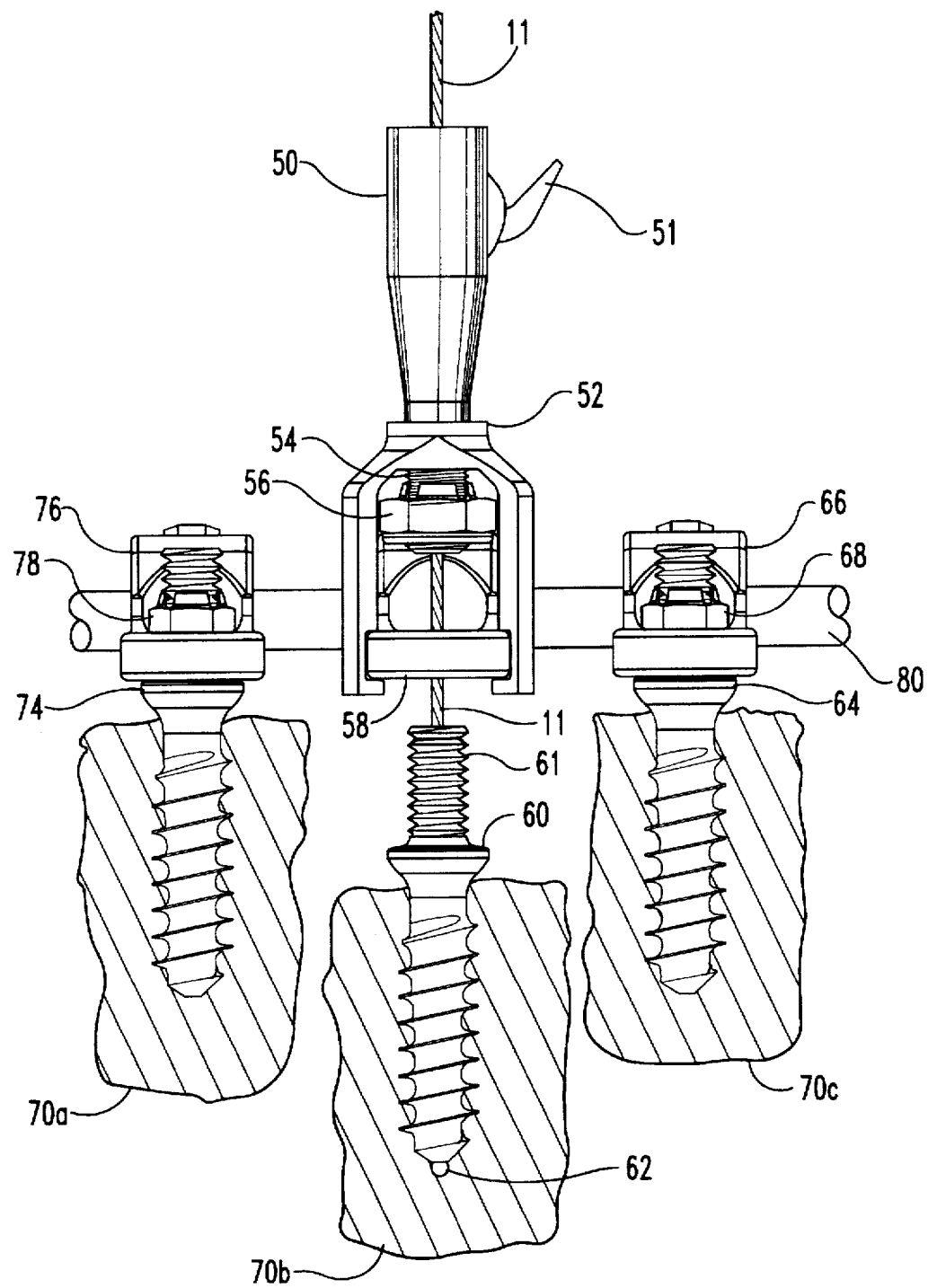
FIG. 2 is a schematic illustration of the application of the cable reduction apparatus according to one embodiment of the invention.
Figure 3:
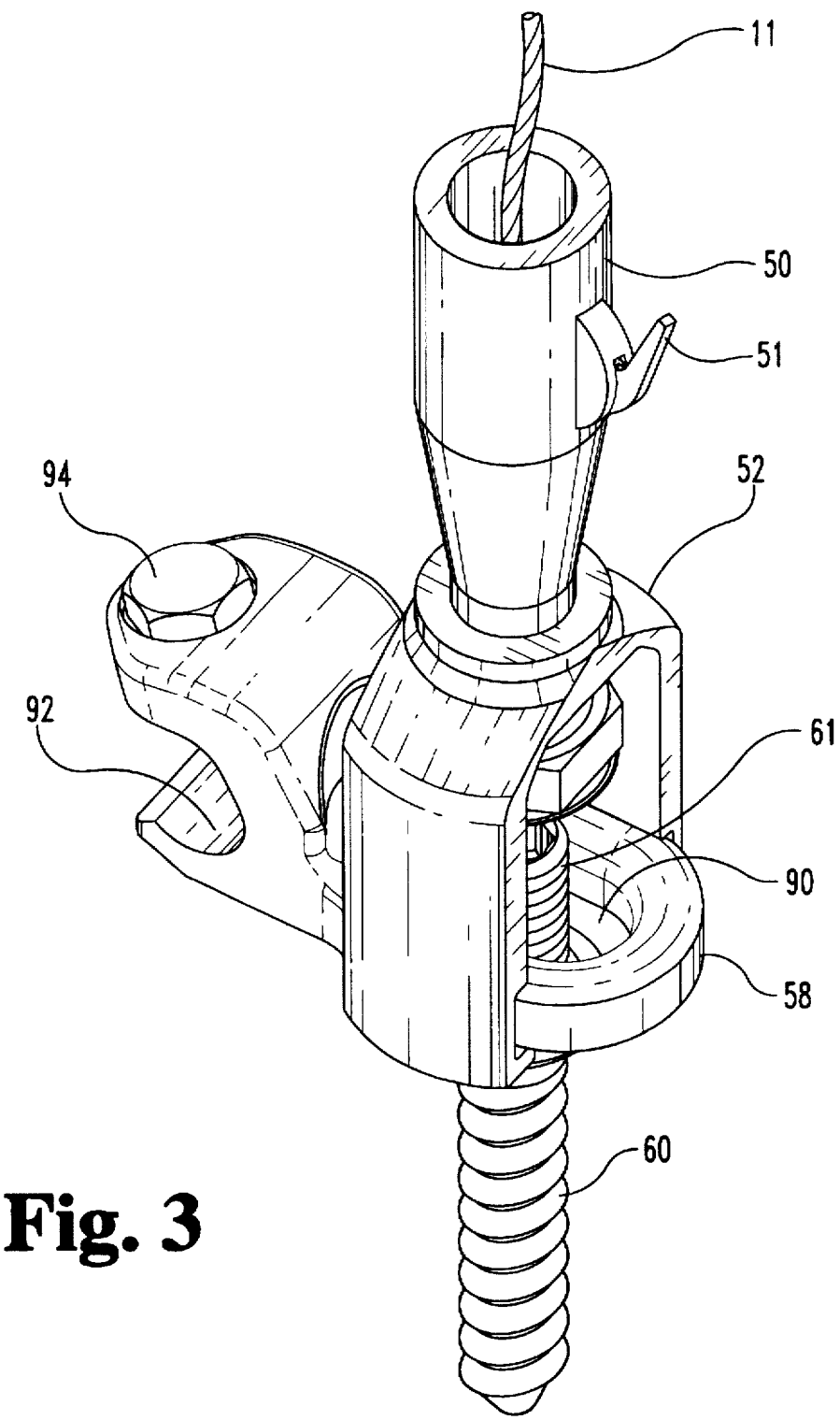
FIG. 3 is a perspective view of the embodiment of the reduction apparatus of FIG. 2.
Figure 4:
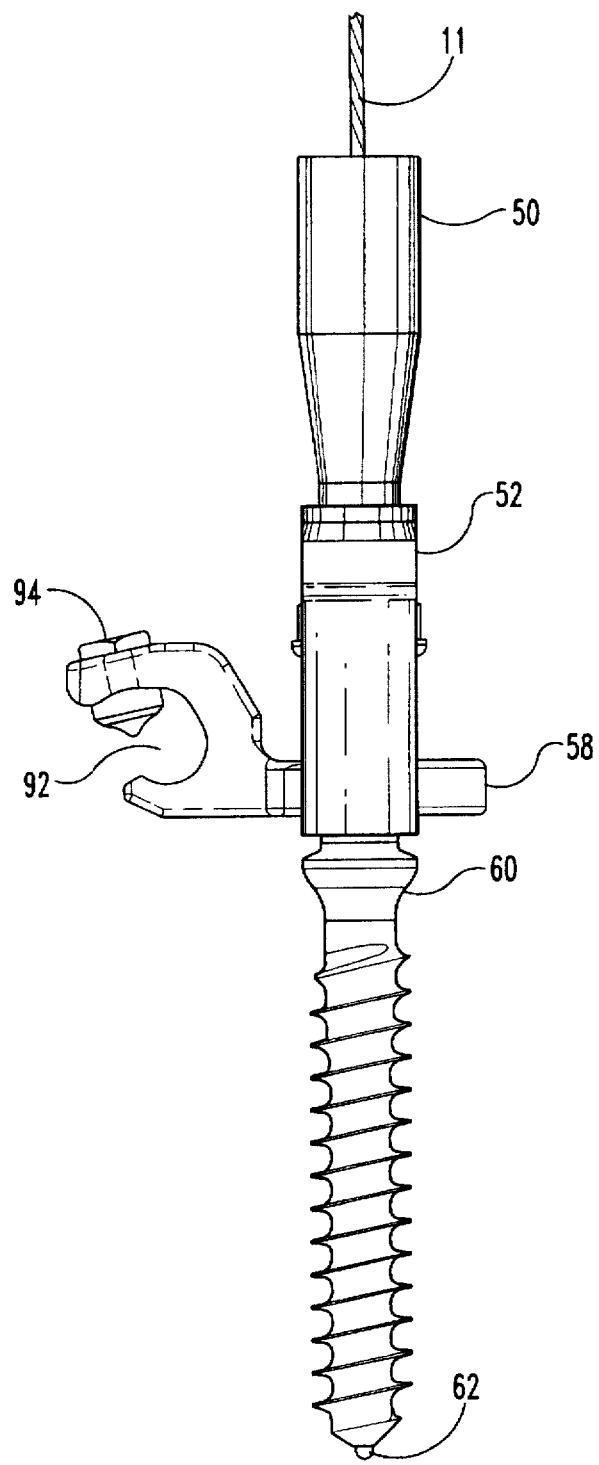
FIG. 4 is a side view of the embodiment shown in FIG. 3.

Referring more specifically now to FIGS. 2 through 4, a reduction apparatus according to one embodiment of the invention is shown. A longitudinal member such as spinal rod 80 spans vertebrae 70a, 70b, and 70c. The rod can be anchored at either end to vertebrae 70a and 70c by a connector assembly consisting of bone bolts 64 and 74 anchored into the respective vertebrae. Rod connector members 66 and 76 are attached to rod 80 and are attached to bone bolts 64 and 74 by machine nuts 68 and 78 respectively. By way of example, the connector assemblies anchoring the rod can include cannulated bolts and rod bolt connectors commercially available from Sofamor Danek with the GDLH® connector system. Although this embodiment utilizes bone bolts and rod connectors to anchor the ends of rod 80, it is contemplated that other means such as hooks or screws, could be used to anchor the rod to the adjacent vertebra to provide a platform for drawing the misaligned vertebra 70b toward rod 80. Moreover, it is contemplated that rod 80 could be substituted by a plate or a rod-plate combination element.

Referring more specifically to the reduction apparatus, an anchoring element such as cannulated bone screw 60 is preferably anchored into intermediate vertebra 70b with the elongated member such as cable 11 extending through the cannula. Cable 11 is maintained in position by an enlargement or ball 62 extending beyond the distal tip of the bone bolt. Ball 62 has a diameter larger than the cannula of bone screw 60, thus preventing passage of the ball through the cannula. Attached to rod 80, is a rod connector 58 having a slot 90 (FIG. 3) disposed therein for receiving machine threaded portion 61 of bone bolt 60. Attached to connector 58 is clamping fixture 52 which can be configured to slide over a portion of rod connector 58. Clamp 50 with clamping lever 51 is similar in design to the clamping apparatus disclosed in U.S. Pat. No. 5,395,374, the disclosure of which is incorporated herein by reference.

Figure 6:
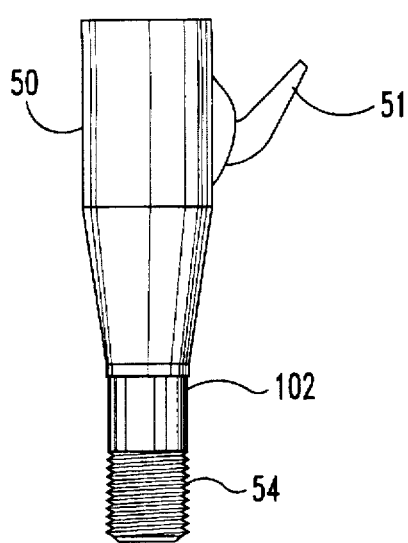
FIG. 6 is a front view of a clamp utilized in the embodiment of FIG. 2.
Figure 7:
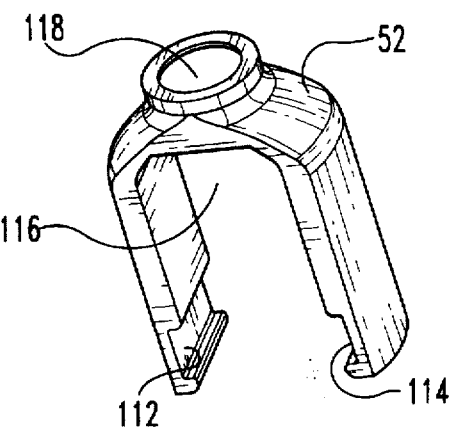
FIG. 7 is a perspective view of a clamp fixture utilized in the embodiment of FIG. 2.

Lower portion 54 of clamp 50 has been modified in the present invention to include an externally threaded portion (FIG. 6). Lower portion 54 is inserted into clamp fixture opening 118 (FIG. 7) such that the threaded portion extends below the clamp fixture and is engaged by internally threaded nut 56. The combination of lower threaded portion 54 on clamp 50 and machine nut 56 operate to securely fasten clamp 50 to clamp fixture 52. Other means of securement are contemplated to support clamp 50 on fixture 52. Clamp fixture 52 is sized such that the machine threaded portion of bolt 60 may be drawn through slot 90 in rod connector 58 a substantial distance without contacting clamp 50. In other words, the fixture 52 supports the clamp 50 above the connector 58 a sufficient distance to provide clearance for the machine threaded portion 61 of the bolt 60.

As illustrated in FIG. 2, cable 11 preferably extends through the cannula of bone bolt 60, through the opening in rod connector 58, and through a passage in clamp 50 so that a proximal end of the cable extends out the upper portion of clamp 50. As will be understood by those skilled in the art, the proximal end of the cable 11 can be threaded through the tensioning tool 17 of FIG. 1 such that the tensioning tool barrel tip 22 abuttingly engages clamp 50. The tool 17 can be used to tension cable 11 to pull vertebra 70b into alignment with the adjacent vertebrae 70a and 70b. Thus, as tensioning force is transmitted to cable 11, tensioning tool 17 engages clamp 50 positioned in fixture 52 engaging the rod connector which ultimately bears against rod 80 anchored to the adjacent vertebrae. In this manner, the tensioning tool uses the rod 80 for leverage to pull the displaced vertebra toward the rod. It is contemplated that for some applications tensioning tool barrel tip 22 could be adapted to directly engage rod 80.

Referring now to FIGS. 3 and 4, the reduction apparatus of FIG. 2 is shown in perspective with bone bolt 60 drawn into slot 90 of the rod connector 58. Additionally, these figures show that rod connector 58 has a passage 92 to accept rod 80 that can be maintained in place on the rod by set screw 94. It is contemplated that any type of rod connector can be acceptable to support a clamping fixture 52 and clamp 50 and that disclosure of the above rod connector is not intended to be limiting in any manner.

Figure 5:
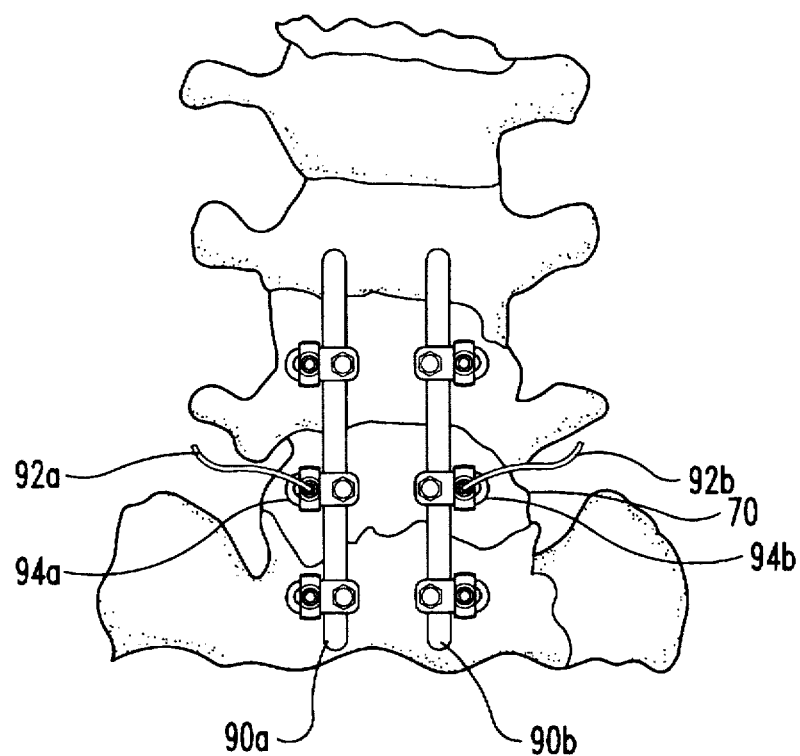
FIG. 5 is a fragmentary dorsal view of a portion of a vertebral column on which an apparatus constructed in accordance with the present invention has been installed.

As shown in FIG. 5, it is contemplated that a pair of spinal rods 90a and 90b can be placed along the spinal column in substantially parallel alignment. For this construct, each rod preferably has a reduction apparatus according to the present invention attached adjacent the misaligned vertebra. Tensioning devices can be attached to each of connectors 94a and 94b such that misaligned vertebra 70 could be reduced by pulling cables 92a and 92b. The tension applied to each cable can be coordinated so that the displaced vertebra 70 can be reduced in the least traumatic manner possible.

Referring now to FIGS. 6 through 9, clamp 50 is shown having a reduced diameter portion 102 adjacent threaded end 54. This portion of reduced diameter is preferably configured to be received within bore 118 of clamp fixture 52 with threaded portion 54 extending into central opening 116. Clamp 50 is provided with channel 126 for receiving the cable and indentation 128 for receiving barrel tip 22 of tensioning tool 17. Furthermore, clamp fixture included means for engaging the rod connector, preferably channels 112 and 114 for slidably engaging connector 58. In the preferred embodiment, the channels 112, 114 are spaced apart and sized to receive the connector 58 therein so the fixture 52 can be readily supported on the connector. Of course, the fixture 52 and/or channels 112, 114 can be modified to accept other types of connectors.

FIGS. 10 and 11 show surgical cable constructions contemplated to be used in conjunction with a reduction apparatus of the present invention. FIG. 10 shows cable 150 with end 156 extending through crimp 152, thereby forming loop 154 at the end of cable 150. Loop 154 is preferably sized with a radius R1 large enough to be passed over the cancellous threads of a bone screw or bone bolt, and small enough to be engaged by the head of a bone screw or the nut of a bone bolt. Once they bone screw/bone bolt is inserted, the cable is secured between the head or seat and the bone. The structure of FIG. 10 is one configuration contemplated to secure a cable to an anchoring element in a vertebra.

Another contemplated cable structure is shown in FIG. 11. Here cable 160 has ball 162 formed at one end. Ball 162 is sized such that cable 160 may pass through an opening and 160 will be retained to effectively attach the cable to an anchoring element or attachment plate.

FIG. 12 shows another embodiment of a cable attached to an anchoring element. Cable 150 with loop 154 formed by crimp 152 is attached to bone screw 180. Loop 154 is passed over the cancellous thread portion 186 of the bone screw and is positioned adjacent the enlarged head 182 of the bone screw. Alternatively, the loop can be larger than the screw head with the crimp 152 being adjustable to allow closing the loop tightly about the shank of the screw 180 below the head 182. The bone screw of FIG. 12 has a splined head which enables the screw to engage a splined washer at a variety of angles, creating numerous angles of attachment. This type of connection is more fully explained in U.S. Pat. No. 5,423,818 and the disclosure is incorporated herein by reference.

Referring now to FIG. 13, bone screw 180 with cancellous portion 186 and enlarged head 182 having splines 184 holds attachment plate 190. Attachment plate 190, more fully shown in FIGS. 14 through 16, has a first large opening 194 at one end sized to pass over threaded portion 186 and is sized to engage the enlarged head of bone screw 180. Attachment plate 190 has a second smaller opening 192 sized to receive cable 160 of FIG. 11, yet small enough to prevent passage of ball 162. This arrangement connects the cable to attachment plate 190. Further, opening 192 can define frustoconical recess 196 which allows cable 160 to be pulled in a variety of angles without engaging an abrupt corner of plate 190. Furthermore, opening 192 can have a spherical recess 198 to engage ball 162 such that the ball may freely rotate within the spherical bore. As a further alternative, large opening 194 can be configured as a clip that resiliently forms to engage the shank of the bone screw.

Referring now to FIG. 17 which illustrates an alternative embodiment of the present invention, cable 214 is threaded through a cannulated bone screw 224 having a splined head 226. Cable 214 has ball 216 located at its distal end which engages the cannulated opening to prevent further movement of the cable through the cannulation of bone screw 224. A T-bolt rod connector 204 can be provided to interconnect bone screw 224 and rod 202 once the vertebra attached to bone screw 224 has been drawn into proper alignment. T-bolt rod connector 204 includes set screw 206 for forcing rod 202 against splined washer 208 which slides along T-bolt shaft 220 to clamp splined head 226 of bone bolt 224 against T-bolt stop 218. Such a configuration can be of the type commercially available as Sofamor Danek's top tightening variable angle TSRH® spinal rod connector system. In an adaptation of that system utilized with the present embodiment the T-bolt shaft 220 can define bore 221 therein for passage of cable 214. Cable 214 passes through bore 221 and can extend through clamp 210 and beyond into tensioning tool 17, shown in FIG. 1. Clamp 210 can include hand operated clamp lug 212 to clamp cable 214 in a desired position. In this embodiment, the clamp 210 preferably rests on the top-tightening T-bolt connector 204 to use the connector 204 for leverage to reduce a vertebra.

Another embodiment of the invention is shown in FIG. 18. In this embodiment, rod 240 is attached to rod connector 242 by set screw 244. Rod connector 242 can have an opening 245 to receive clamp 246, more particularly a reduced diameter portion 248. The rod connector 242 can be specially configured to support clamp 246, or the clamp 246 can be configured to engage a known rod connector. Here again, clamp 246 has a hand-operator clamp lug 250 to clamp cable 252 in a desired position. Cable 252 has loop 254 formed at its distal end which is attached to bone screw 256. Unlike the embodiments shown in FIGS. 3 and 17, once the tensioning apparatus has drawn the misaligned vertebra into approximately the desired position, rod connector 242 can be removed from the rod and replaced with a rod connector of a variety suitable to attach the bone screw 256 to the rod. Although the splined bone screw is utilized for illustration in this embodiment, it is contemplated that the anchoring element in the vertebrae could be formed of a variety of anchoring types, any of which could be connected to the rod.

In a further embodiment of the invention, FIG. 19 shows a connector member 272 similar to that shown in FIG. 18 attached to rod 207 by set screw 274. Here again, connector 272 has an opening 275 for receiving clamp 276. In this embodiment, attachment plate 284 is positioned between the bone screw cancellous threads 286 and the head portion 288. The attachment plate is similar to that shown in FIGS. 14 through 16. In this embodiment, cable 280 is passed through openings 283 and attachment plate 284 and cable ball 282 engages the opening. thereby drawing the plate and bone screw toward clamp 276 when a pulling force is applied to cable 280.

It will be understood by those skilled in the art that while a separate cable clamp has been shown in each embodiment, this clamp could be replaced by a tensioning tool with an integral clamp or removable clamp adaptor such that the tensioning tool would directly engage the rod connector. Additionally, it is contemplated that tensioning tool barrel tip could directly engage the rod connector if clamping of the cable is not required.

Although it is contemplated that an anchor element could first be secured to the misaligned vertebra and then have a cable secured to the anchor, the cable can be secured to the bone screws prior to insertion into the vertebra. After insertion of the bone screw with attached cable, additional anchors are implanted in adjacent vertebrae such that the rod may be anchored prior to the tensioning process.

Referring specifically to FIG. 2, cannulated bone bolt 60 with attached cable can be inserted into vertebra 70b. Bone bolts 64 and 74 can then be inserted into adjacent vertebrae 70c and 70a, respectively. Rod connectors 66 and 76 can then be secured to rod 80 and nuts 68 and 78 are threaded onto bone bolt 64 and 74, respectively, to clamp the rod connectors to the bone bolts. Once the rod has been sufficiently secured, connectors 58 is secured to the rod by placing the rod into opening 92 of connector 58 and then tightening set screw 94 until the rod is grasped securely. Clamp 50 is inserted through bore 118 and secured to clamp fixture 52 by threading nut 56 on a threaded portion 54.

Cable 11 is then threaded through rod connector slotted opening 90 and through clamp opening 126. Clamp fixture 52 is then slidingly engaged onto rod connector 58 by sliding the bolt portion of connecting connector 58 along channels 112 and 114. Once these components are in position, cable 11 can be positioned in tensioning tool 17. Once cable 11 has been threaded through the tensioning tool and barrel tip 22 is in contact with clamp 50, clamp lug 18 is tightened to securely hold the cable within the tensioning tool. Any slack in cable 11 can then be removed by holding the barrel 20 of the tensioning tool and pulling portion 19 away from barrel 20. Tension is then applied to cable 11 by depressing hand lever 21 repeatedly until the desired level of tension is achieved, as indicated by scale 26.

As shown in FIG. 5, it is contemplated that a reduction apparatus according to the present invention would be positioned on each of a pair of rods placed along the longitudinal axis of the spine. Tension can first be applied to one side and then applied to the opposite side, thereby slowly working the vertebra into the desired position. According to the present invention, a separate tensioning tool could be used on each tensioning apparatus. Alternatively, clamp 50 may be engaged, thereby clamping the cable in a desired position and tensioning tool 17 removed and positioned on the opposite side to apply tension. This process of tensioning one side and moving the tensioning tool can be repeated as needed.

Once threaded portion 61 is positioned in slot 90, internally threaded nut 56 can be threaded over machine threaded portion 61 and tightened until rod connector 58 is clamped between the enlarged seat portion of bone bolt 60 and the machine threaded nut. After this procedure is accomplished, tensioning tool 17, clamp 50, and fixture 52 of the tensioning apparatus are removed. Cable 11 is cut as close to the bone bolt as practicable, leaving a portion of the cable in the patient. This operation is then repeated on the other side of the vertebra, thereby completing the reduction procedure.

For the embodiment shown in FIG. 17, once the vertebra is drawn into the desired position, set screw 206 can be tightened until splined washer 208 firmly holds splined head 226 against T-bolt stop 218. Clamp 210 is then removed and cable 214 is cut as close to the head of the bone screw as practicable.

For the embodiments shown in FIGS. 18 and 19, the vertebra displacement is reduced, the cable is cut and the tensioning components are removed along with the rod connector. A rod connector suitable for attachment to the splined screw head is then attached to the rod and the splined screw head is attached to the connector in a conventional fashion.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for use in reducing a displaced vertebra in the spine, said apparatus comprising:

a longitudinal member positionable along the longitudinal axis of a spine;

an anchor configured to be secured to a displaced vertebra;

an elongated member having a first portion attached to said anchor and a second portion;

a clamping member positionable along said longitudinal member adjacent the displaced vertebra said clamping member defining a channel for receiving said second portion of said elongated member, said clamping member operable between an open configuration permitting movement of said elongated member through said channel and a clamping configuration engaging said elongated member to prevent movement of said elongated member through said channel; and means for pulling said elongated member through said channel, whereby the displaced vertebra can be pulled toward said longitudinal member.

2. The apparatus of claim 1, wherein said longitudinal member is an elongated rod and said means for pulling includes means for engaging said rod.

3. The apparatus of claim 2, wherein said rod engaging means is a rod connector, said clamping member engages said rod connector, and said means for pulling leverages against said clamping member.

4. The apparatus of claim 3 further including a clamp fixture adapted to engage said rod connector and maintain said clamp a spaced distance from said rod connector, said fixture having a lower portion engaging said rod connector and an upper portion adapted to receive said clamp.

5. The apparatus of claim 1, wherein said longitudinal member has two ends, each of which is anchorable to the spine to prevent movement of said longitudinal member relative to the spine.

6. The apparatus of claim 1, wherein said anchor is a bone bolt having a first portion for threadedly engaging bone, a second portion for threadedly engaging an internally threaded nut, and a central portion located between said first and second portions defining an enlarged seat.

7. The apparatus of claim 6 wherein said bone bolt further defines an axial cannula of a first diameter and said elongated member has a second diameter smaller than said first diameter and an enlarged end having a third diameter larger than said first diameter of said cannula, said elongated member extending through the cannula of said bone bolt and maintained in position by said enlarged end engaging said bone bolt adjacent the first portion.

8. The apparatus of claim 1, wherein said anchor is an externally threaded bone screw.

9. The apparatus of claim 8 wherein said bone screw defines an axial cannula of a first diameter, and said elongated member has a second diameter smaller than said first diameter and an enlarged end having a third diameter larger than said first diameter of said cannula, said elongated member extending through the cannula of said screw and maintained in position by said enlarged end engaging said screw.

10. The apparatus of claim 8, wherein said elongated member is a cable defining a loop of a first diameter at one end, and said bone screw having an enlarged head at one end and a threaded shank having a second diameter smaller than said first diameter, said enlarged head having a third diameter larger than said first diameter, whereby said loop is positioned about said threaded portion and engages said enlarged head.

11. The apparatus of claim 8 wherein said screw includes an enlarged head at one end and said elongated member is a cable with an enlarged end, and further including an attachment plate having two ends and a hole positioned at each end, one hole sized to receive the threaded portion of said bone screw and engage the enlarged head and the other hole sized to receive the cable and engage the enlarged end.

12. The apparatus of claim 1, wherein said elongated member is a cable.

13. The apparatus of claim 1, wherein said elongated member is flexible.

14. The apparatus of claim 13, wherein said elongated member is a cable.

15. The apparatus of claim 1, wherein said clamp member defines a fully enclosed channel surrounding said elongated member.

16. The apparatus of claim 15 wherein said enclosed channel is cylindrical.

17. An apparatus for reducing a displaced vertebra in the spine, said apparatus comprising:
a longitudinal member positionable along the longitudinal axis of a spine;
an anchor configured to be secured to a displaced vertebra;
an elongated member having a first end attached to said anchor and a second end;
a clamping member positionable along said longitudinal member adjacent the displaced vertebrae and engaging a portion of said elongated member between said first end and said second end, said clamping member operable to selectively clamp said elongated member;
means for pulling said elongated member toward said clamping member, whereby the displaced vertebra can be pulled toward said longitudinal member; and
said clamping member includes a lever for operating said clamping member between an open position permitting free movement of said elongated member and a clamping position clamping said elongated member in a stationary position.

18. An apparatus for use in reducing a displaced vertebra of the spine, said apparatus comprising:
a longitudinal member positionable along the longitudinal axis of the spine;
means for engaging a displaced vertebrae;
a flexible elongated member having a first portion connected to said engaging means and a second portion;
means for securing said flexible elongated member positionable along said longitudinal member adjacent the displaced vertebra, said means for securing having a channel for slidably receiving said flexible elongated member and operable to selectively engage said second portion of said elongated member to prevent movement of the vertebrae away from said longitudinal member; and
means for pulling said elongated member through said channel, thereby the displaced vertebra can be pulled toward said longitudinal member.

19. An apparatus for use in reducing a displaced vertebra in the spine, said apparatus comprising:
a longitudinal member positionable along the longitudinal axis of the spine;
an anchor secured to a displaced vertebra;
a flexible elongated member attached to said anchor; and
a tensioning tool positionable along said longitudinal member adjacent the displaced vertebra, said tensioning tool including a gripping portion for gripping said elongated member and a bearing portion for bearing against said longitudinal member, said gripping portion moveable with respect to said bearing portion.

20. The apparatus of claim 19, wherein said longitudinal member is an elongated rod, and further including a rod connector attached to said rod and a clamp connected to said rod connector, said clamp defining an opening for receiving said elongated member and said tensioning tool bearing against said clamp thereby pulling said elongated member through said clamp and drawing said anchor toward said rod.

21. The apparatus of claim 20 further including a clamp fixture adapted to engage said rod connector and maintain said clamp a spaced distance from said rod connector, said fixture having a lower portion engaging said rod connector and an upper portion adapted to receive said clamp.

22. An apparatus for use in reducing a displaced vertebra in the spine, said apparatus comprising:
a longitudinal member positionable along the longitudinal axis of the spine;
means for engaging a vertebra;
a flexible elongated member attached to said engaging means; and p1 means for pulling said elongated member, said means including a gripping portion for gripping said elongated member and a bearing portion for bearing against said longitudinal member, said gripping portion moveable with respect to said bearing portion, whereby movement of said gripping portion with respect to said bearing portion pulls said engaging means towards said longitudinal member.

23. A method for aligning a displaced vertebra, comprising the steps of:
connecting a flexible elongated member to an anchoring element;
attaching the anchoring element to a displaced vertebra;
positioning a longitudinal member along the longitudinal axis of the spine;
positioning a clamping device having a channel to bear against the longitudinal member;
threading an end of the elongated member opposite the anchoring element through the channel of the clamping device;

pulling the elongated member to move the elongated member through the channel of the clamping device, thereby moving the displaced vertebra toward the longitudinal member; and clamping the elongated member to maintain the vertebra in a desired position.

24. The method of claim 23, wherein the elongated member is a cable having an enlarged end and the anchoring element is externally threaded and includes an axial cannula and an end, and the step of connecting the elongated member to the anchoring element is performed by threading the cable through the cannula of the anchoring element until the enlarged end engages the end of the anchoring element.

25. The method of claim 23, wherein the elongated member is a cable having an enlarged end and the anchoring element is a bone screw having a threaded portion and an enlarged head and further includes an attachment plate having a first opening and a second opening, the step of connecting the elongated member to the anchoring element comprising the steps of inserting the threaded end of the bone screw through the first opening in the attachment plate until the enlarged head engages the attachment plate and threading the cable through the second opening in the attachment plate until the enlarged end engages the attachment plate.

26. The method of claim 23, wherein the elongated member is a cable having a looped formed at one end and the anchoring element is a bone screw having an enlarged head, the step of connecting the elongated member to the anchoring element is performed by inserting the bone screw into the cable loop until the enlarged head engages the cable.

27. The method of claim 23, wherein the longitudinal member is an elongated rod and positioning the clamping device includes securing a rod connector to the rod and positioning the clamping device in engagement with the rod connector.

28. A method for aligning a displaced vertebra, comprising the steps of:

connecting an elongated member to an anchoring element;

attaching the anchoring element to a displaced vertebra;

positioning a longitudinal member along the longitudinal axis of the spine;

positioning a clamping device to bear against the longitudinal member;

threading an end of the elongated member opposite the anchoring element through the clamping device;

pulling the elongated member to move the elongated member through the clamping device, thereby moving the displaced vertebra toward the longitudinal member;

clamping the elongated member to maintain the vertebra in a desired position;

removing the clamping device;

cutting the elongated member adjacent the anchoring element; and interconnecting the anchoring element and the longitudinal member to maintain the vertebra in the desired position.

29. A method for aligning a displaced vertebra, comprising the steps of:

connecting an elongated member to an anchoring element;

attaching the anchoring element to a vertebra;

positioning a longitudinal member along the longitudinal axis of the spine;

positioning a tensioning tool to bear against the longitudinal member;

grasping the elongated member with the tensioning tool; and pulling the elongated member toward the longitudinal member and into a desired position.

30. The method of claim 29, further including the steps of removing the tensioning tool after the vertebrae is in the desired position, cutting the elongated member adjacent the anchoring element and interconnecting the anchoring element and the longitudinal member to maintain the vertebra in the desired position.

31. An apparatus for use in the spine, said apparatus comprising:

an elongated rod positionable along the longitudinal axis of a spine;

an anchor configured to be securable to a vertebra;

an elongated member having a first portion attached to said anchor and a second portion;

a rod connector adapted to engage said rod and positionable along said rod adjacent said vertebra;

a clamping member operable to selectively clamp said elongated member, said clamping member including a threaded end;

a clamp fixture adapted to engage said rod connector and to maintain said clamping member a spaced distance from said rod connector, said fixture having a lower portion adapted to engage said rod connector and an upper portion having an axial bore therein adapted to receive said clamping member, said clamp fixture defining a central opening between said lower portion and said upper portion;

means for pulling said elongated member toward said clamping member, thereby pulling the vertebra toward said longitudinal member; and a threaded nut adapted to engage said threaded end of said clamping member, wherein said threaded end extends through said axial bore into said central opening of said clamping fixture, said threaded nut engages said threaded end to maintain said clamping member in position and said lower portion of said clamp fixture engages said rod connector.

\* \* \* \* \*

UNITED STATES PATENT AND TRADEMARK OFFICE
CERTIFICATE OF CORRECTION

PATENT NO : 5,782,831
DATED : July 21, 1998
INVENTOR(S): Michael C. Sherman and Troy D. Drewry It is certified that error appears in the above-identified patent and that said Letters Patent is hereby corrected as shown below:

On the title page, item [54] and col.1, line 1, delete "AN" and insert --AND--.

Column 2, line 2, delete the word "placed".

Column 3, line 2, after the words "in the", delete the word "and".

Column 6, line 50, change numeral "3" to --2--.

Column 7, line 28, change "connectors" to --connector--.

Column 10, line 13, change "thereby" to --whereby--.

Column 10, line 47, delete "P1" and insert a new paragraph beginning with the word "means"

Signed and Sealed this

Tenth Day of August, 1999

Attest:

Q. TODD DICKINSON

*Attesting Officer*     *Acting Commissioner of Patents and Trademarks*